United States Patent [19]

Grosvenor et al.

[11] Patent Number: 4,889,940

[45] Date of Patent: Dec. 26, 1989

[54] PROCESS FOR PREPARING THIOPHENE DERIVATIVES

[75] Inventors: Peter R. Grosvenor, Wolverhampton; Lance S. Fuller, Acton Trussell, both of England

[73] Assignee: Shell Internationale Research Maatschappij B.V., The Hague, Netherlands

[21] Appl. No.: 205,647

[22] Filed: Jun. 13, 1988

[30] Foreign Application Priority Data

Jul. 14, 1987 [GB] United Kingdom ................ 8716587

[51] Int. Cl.$^4$ ........................................... C07D 333/28
[52] U.S. Cl. ..................................................... 549/81
[58] Field of Search .......................................... 549/81

[56] References Cited

U.S. PATENT DOCUMENTS 4,417,081 11/1983 Soula .................................. 570/147
4,629,815 12/1986 Soula .................................. 570/202

FOREIGN PATENT DOCUMENTS 8542881 5/1985 Australia.

OTHER PUBLICATIONS

Dettmeier, U., et al., Angew. Chem. Int. Ed. Engl. 26 (1987) No. 5, pp. 468–469.
Reinecke, M. G., et al., J. Amer. Chem. Soc., 90, 511-13 (1968).
Reinecke, M. G., et al. J. Org. Chem., vol. 36, No. 18, 2690-2692 (1971).
Soula, G., J. Org. Chem. 50, 3717-3721 (1985).
TDA-1 Catalog, Rhone-Poulenc Division Specialites Chimiques, Doc. (1) 47 88 17 15.
Van der Plas, H. C., et al., Recueil 93, 33-36 (1974).
Dettmeier, U., et al., Angew. Chem. Int. Ed. Engl. 26 (1987), No. 5, p. 468.
Gronowitz, S., Heterocyclic Chemistry, Thiophene and its Derivatives, vol. 44, part 2, p. 243.
Organic Synthesis, vol. 44, pp. 9-11.

*Primary Examiner*—Alan Siegel

[57] ABSTRACT

A process for the preparation of a thiophene derivative which is substituted at the beta-position by a bromine atom, which comprises reacting the corresponding beta-unsubstituted thiophene with an aromatic compound which is substituted with a bromine atom, in the presence of an alkali metal amide and a catalyst which is capable of forming a complex with the cation of the alkali metal amide.

10 Claims, No Drawings

PROCESS FOR PREPARING THIOPHENE DERIVATIVES

The present invention relates to a process for the preparation of certain beta-substituted thiophene derivatives from the corresponding beta-unsubstituted thiophenes.

Reinecke M.G. et al, J. Org Chem., Vol 36, No. 18, 1971, pages 2690 to 2692 describe a process for the preparation of certain beta-bromothiophenes from alpha-bromothiophenes using sodium or potassium amide in liquid ammonia. While the process works well on a laboratory scale, it would be extremely difficult to perform on a commercial scale because of the difficulty of handling liquid ammonia.

Surprisingly we have now found an advantageous process for the preparation of certain beta-bromothiophenes which does not require liquid ammonia.

Accordingly, the present invention provides a process for the preparation of a thiophene derivative which is substituted at the beta-position by a bromine atom, which comprises reacting the corresponding beta-unsubstituted thiophene with an aromatic compound which is substituted with a bromine atom, in the presence of an alkali metal amide and a catalyst which is capable of forming a complex with the cation of the alkali metal amide.

The aromatic compound is preferably a thiophene derivative, for example 2-bromothiophene, 2,5-dibromothiophene, 2,3,5-tribromothiophene or 2,3,4,5-tetrabromothiophene. The use of 2-bromothiophene or 2,5-dibromothiophene is preferred. However the aromatic compound can be other than a thiophene, such as a polybromobenzene; e.g. a tetrabromobenzene, a pentabromobenzene or hexabromobenzene.

It will be appreciated that mixtures of aromatic compounds may be used. This may be particularly advantageous when the process used to prepare the aromatic compounds affords them in such a mixture, since a separation step is then not needed.

The beta-unsubstituted thiophene may be unsubstituted or substituted by one or more substituents which do not take part in the reaction, for example by a halogen atom such as a chlorine or bromine atom, an alkyl group such as a methyl group, or a nitrile group. Alternatively the thiophene portion of the beta-unsubstituted thiophene may be fused to another aromatic ring, for example as in benzo[b]thiophene. Preferably the beta-unsubstituted thiophene is thiophene itself.

In some cases, the beta-unsubstituted thiophene and the aromatic compound may be the same compound.

It will be appreciated that when both beta-positions of the beta-unsubstituted thiophene are unsubstituted, then it is possible to obtain a product which is mono- or disubstituted at the beta position. For example, 3-bromothiophene can be obtained by reacting an excess of thiophene with an alpha-bromothiophene such as 2-bromothiophene or 2,5-dibromothiophene, for example using from 3 to 7 moles of thiophene per mole of alpha-bromothiophene, and 3,4-dibromo- thiophene may be prepared by reacting 2,5-dibromothiophene with itself.

The alkali metal amide employed in the process according to the invention may be, for example, a sodium or potassium amide. The amount of alkali metal amide employed in the process is not critical, but is preferably in the range of from 0.5 to 5 moles per mole of migrating substituent, more preferably from 1.5 to 3 moles.

The catalyst may, for example, be a polyether. One suitable class of polyethers includes compounds of the general formula

$$(R^1\text{-}(O\text{-}CHR^2\text{-}CHR^3)_m\text{-}O\text{-}CHR^4\text{-}CHR^5)_3N \qquad (I)$$

in which $R^2$, $R^3$, and $R^5$ are independently selected from a hydrogen atom and an alkyl group having up to 4 carbon atoms; $R^1$ represents an alkyl, cycloalkyl, phenyl, phenylalkyl or alkylphenyl group in which any alkyl or cycloalkyl group has up to 12 carbon atoms; and m is 0 or an integer from 1 to 10.

Another suitable class of polyethers includes linear polyethers of the general formula

$$R^6\text{-}(O\text{-}R^8)_r\text{-}O\text{-}R^7 \qquad (II)$$

in which $R^6$ and $R^7$, which may be the same or different, each represents a hydrogen atom or an alkyl group having from 1 to 4 carbon atoms; in each $O\text{-}R^8$ unit, which may be the same or different, $R^8$ independently represents a group selected from $CHR^9CHR^{10}$ and $CHR^9CHR^{10}CR_{11}R^{12}$ in which $R^9$, $R^{10}$, $R^{11}$ and $R^{12}$ are independently selected from a hydrogen atom and an alkyl group having from 1 to 4 carbon atoms; and r represents an integer of from 1 to 15. For example the compound of formula II may be ethylene glycol.

The compounds of formulae (I) and (II) are known.

More preferably, the catalyst is tris(3,6-dioxaheptyl)amine or tris(3,6-dioxaoctyl)amine.

The amount of catalyst employed in the process according to the invention will depend upon the chosen reaction conditions and the particular catalyst which has been selected. Generally the amounts will be in the range of from 0.5 to 5 grammes per mole of migrating substituent, preferably 0.75 to 1.5 grammes per mole.

The process according to the invention may conveniently be effected at a temperature in the range of from 10° to 90° C., preferably from 40° to 70° C. It will be appreciated that the process described by Reinecke M. G. et al, J. Org Chem., Vol 36; No. 18, 1971, pages 2690 to 2692 requires very low temperatures. Thus it is particularly advantageous that the process according to the invention may be performed at a temperature in the range of from 10 to 90° C. Conveniently the process is effected under an inert atmosphere such as nitrogen gas.

The process may, if desired, be effected in the presence of an inert solvent. However, it is preferable to effect the process in the presence of an excess of the beta-unsubstituted thiophene; for example the molar ratio of beta-unsubstituted thiophene to aromatic compound may be in the range of from 1:1 to 25:1, preferably from 5:1 to 15:1.

Suitable inert solvents which may be employed in the process according to the invention include ethers; e.g. tetrahydrofuran, dioxan or diethyl ether, and aromatic hydrocarbons; e.g. toluene. Toluene is preferred when a solvent is used.

The work up of reaction mixtures may be effected by standard methods of organic chemistry, e.g., quenching, then solvent extraction or steam distillation followed by fractional distillation.

The beta-substituted thiophene derivatives preparable by the process according to the invention are useful as intermediates in the preparation of pharmaceutical compounds. For example, 3-bromothiophene may be used to prepare 3-thienyllithium which may itself be used to prepare the vasodilator, Tinofedrine as described in Drugs of the Future, 1979, Vol 4, 286–290. 3,4-Dibromothiophene may be used in the preparation of conducting polymers, as described by G. Tourillon and F. Garnier in J. Electro. Anal. Chem; 1984, vol 161, part 1, pages 51 to 58. 3-Bromo-4-methylthiophene is useful in the preparation of pharmaceuticals, as described in European patent application EP 53603.

The following Examples illustrate the invention.

EXAMPLE 1

Preparation of 3-bromothiophene using 2,5-dibromothiophene 2,5-Dibromothiophene (24.2 g, 0.1 mole), tris (3,6-dioxaheptyl) amine (0.1 g, 0.0003 mole), thiophene (60 cm$^3$) and sodium amide (23.4 g, 0.6 mole) were successively charged to a 250cm$^3$ three-necked round bottomed flask which had previously been purged with dry nitrogen gas for 1 hour. The reaction mixture was stirred and heated under nitrogen at 50°–60 C. for 4 hours. The reaction mixture was queched with butan-1-ol and then water. The organic layer was separated and the aqueous layer extracted with dichloromethane. The organic layer, after dichloromethane and thiophene removal by distillation, yielded 28.4 g of product. Analysis of the product by gas chromatography with internal standard showed the sample to be mainly monobromo thiophenes in the ratio 2 parts 2-bromothiophene to 98 parts 3-bromothiophene.

3-Bromothiophene has the following physical characteristics:

Boiling Point 95° C. at 100 mm Hg.
'H nmr (CCl$_4$,TMS).
$\delta$/ppm: 6.91–7.20 (m, H2, H4, H5).

EXAMPLE 2

Preparation of 3-bromothiophene using 2-bromothiophene

2-Bromothiophene (16.3 g, 0.1 mole), tris (3,6-dioxaheptyl)amine (0.1 g, 0.0003 mole), thiophene (50 cm$^3$) and sodium amide (7.8 g, 0.2 mole) were successively charged to a 250 cm$^3$ three-necked round bottomed flask which had previously been purged with dry nitrogen gas for 1 hour. The reaction mixture was stirred and heated under nitrogen at 50°–60° C. for 12 hours. The reaction mixture was quenched with butan-1-ol and then water. The organic layer, after dichloromethane and thiophene removal, yielded 19.4 g of product. Analysis of the product by gas chromatography with internal standard showed the sample to be mainly monobromothiophenes in the ratio 3 parts 2-bromothiophene to 97 parts 3-bromothiophene.

EXAMPLE 3

Preparation of 3-bromothiophene using 2,5-dibromothiophene

Sodium amide (11.7 g, 0.3 mole) and thiophene (100cm$^3$) were charged to a 250 cm$^3$ three—necked round bottomed flask which had previously been purged with dry nitrogen gas for 1 hour. 2,5-dibromothiophene (24.2 g, 0.1 mole) and tris (3;6-dioxaheptyl) amine (0.1 g, 0.0003 mole) were added over 5–10 minutes. The reaction mixture was stirred and heated under nitrogen at 50°–60° C. for 6 hours.

After cooling to 25° C. methanol (14 g, 0.4375 mole) was added over 1 hour to quench the sodium amide.

Water (50 cm$^3$) was added and the organic layer steam distilled out. The organic layer was separated from the water and analysed by gas chromatography. The product (113.9 g) was found to contain 22.7% 3-bromothiophene and 0.8% 2-bromothiophene, the remainder being thiophene and methanol, this is equivalent to a yield of 79% to 3-bromothiophene.

EXAMPLE 4

Preparation of 3-bromothiophene using 2,5-dibromothiophene 2,5-Dibromothiophene (121 g, 0.5 moles), tris (3,6-dioxaheptyl) amine (1.0 g, 0.003 mole), thiophene (500 cm$^3$) and sodium amide (58.5 g, 1.5 mole) were successively charged to a flask which had previously been purged with nitrogen. The reaction mixture was stirred and heated under nitrogen at 50°–60° C. for 6 hours. The product, after work up as described in Example 3, was found to contain 138.5 g 3-bromothiophene and 2.6 g 2-bromothiophene. The yield of 3-bromothiophene was 85% and the monobromothiophenes were in the ratio of 2 parts 2-bromothiophene to 98 parts 3-bromothiophene.

EXAMPLE 5

Preparation of 3-bromothiophene using 2,3,5-tribromothiophene 2,3,5-tribromothiophene (21.2 g, 0.07 moles), tris (3,6-dioxaheptyl) amine (0.2 g, 0.0006 mole), thiophene (120 cm$^3$) and sodium amide (11.7 g, 0.3 mole) were successively charged to a flask which had previously been purged with nitrogen. The reaction mixture was stirred and heated under nitrogen at 50°–60° C. for 6 hours. The product, after work up as described in Example 3, was found to contain 20.4 g 3-bromothiophene and 0.8 g 2-bromothiophene. The yield of 3-bromothiophene was 63% and the monobromothiophenes were in the ratio of 4 parts 2-bromothiophene to 96 parts 3-bromothiophene.

EXAMPLE 6,

Preparation of 3-bromothiophene using 2,3,4,5-tetrabromothiophene 2,3,4,5-tetrabromothiophene (20 g, 0.05 moles), tris (3,6-dioxaheptyl) amine (0.2 g, 0.0006 mole), thiophene (140 cm$^3$) and sodium amide (11.7 g, 0.3 mole) were successively charged to a flask which had previously been purged with nitrogen. The reaction mixture was stirred and heated under nitrogen at 50°–60 C. for 6 hours. The product, after work up as described in Example 3, was found to contain 24.6 g 3-bromothiophene and 0.8 g 2-bromothiophene. The yield of 3-bromothiophene was 75% and the monobromothiophenes were in the ratio of 3 parts 2-bromothiophene to 97 parts 3-bromothiophene.

EXAMPLE 7

Preparation of 3-bromo-4-methylthiophene using 2,5-dibromo-3-methylthiophene 2,5-dibromo-3-methylthiophene (25.6 g, 0.1 mole), tris (3,6-dioxaheptyl) amine (0.2 g, 0.0006 mole), 3-methylthiophene (100cm$^3$) and sodium amide (11.7 g, 0.3 mole) were successively charged to a flask which had previously been purged with nitrogen. The reaction mixture was stirred and heated under nitrogen at 50°–60° C. for 6 hours. The product, after work up as described in Example 3 was found to contain 14.2 g 3-bromo-4-methylthiophene, a yield of 43%.

3-Bromo-4-methylthiophene has the following physical characteristics:

boiling point 114° C. at 100 mm Hg.

$^1$H nmr (CCl$_4$, TMS) δ/ppm: 7.12, 7.06 (d, H2, J=2HZ), 6.86(m, H5), 2.10 (s, CH$_3$)

EXAMPLE 8

Preparation of 3-bromothiophene using ethylene glycol as catalyst 2,5-dibromothiophene (24.2 g, 0.1 mole), ethylene glycol (0.5 g, 0.008 mole), thiophene (100 cm$^3$) and sodium amide (11.7 g, 0.3 mole) were successively charged to a flask which had previously been purged with nitrogen. The reaction mixture was stirred and heated under nitrogen at 50°–60° C. for 6 hours. The product, after work up as described in Example 3, was found to contain 9.1 g 3-bromothiophene and 16 g 2-bromothiophene. The yield of 3-bromothiophene was 29% and the monobromothiophenes were in the ratio of 64 parts 2-bromothiophene to 36 parts 3-bromothiophene.

EXAMPLE 9

Preparation of 3-bromothiophene using toluene as a solvent 2,5-Dibromothiophene (24.2 g, 0.1 mole), tris (3,6-dioxoheptyl) amine (0.2 g, 0.0006 mole), toluene (90 cm$^3$), thiophene (9.5 cm$^3$) and sodium amide (11.7 g, 0.3 mole) were successively charged to a flask which had previously been purged with nitrogen. The reaction mixture was stirred and heated at 50°–60° C. under nitrogen for 6 hours. The product was found to contain 13.3 g 3-bromothiophene and 0.9 g 2-bromothiophene. The yield of 3-bromothiophene was 41% and the monobromothiophenes were in the ratio of 7 parts 2-bromothiophene to 93 parts 3-bromothiophene. Work up was effected by the addition of water and methanol, followed by filtration. The filtrate separated into two layers; the organic layer containing the title compound.

EXAMPLE 10

Preparation of 3,4-dibromothiophene using 3-bromothiophene 2,5-Dibromothiophene (24.2 g, 0.1 mole), tris (3,6-dioxoheptyl amine (0.2 g, 0.0006 mole), 3-bromothiophene (100cm$^3$) and sodium amide (11.7 g, 0.3 mole) were successively charged to a flask which had previously been purged with nitrogen. The reaction mixture was stirred and heated at 50°–60° C. under nitrogen for 6 hours. The product, after work up as described in Example 3, was found to contain 25.5 g 3,4-dibromothiophene, an apparent yield of 105% based on the 2,5-dibromothiophene.

3,4-Dibromothiophene has the following physical characteristics:

boiling point 111° C. at 20 mm Hg.

$^1$H nmr (CCl$_4$, TMS) δ/ppm: 7.17 (s, H2 and H5).

EXAMPLE 11

Preparation of 3,4-dibromothiophene using tetrahydrofuran as solvent 2,5-Dibromothiophene (24.2 g, 0.1 mole), tris (3,6-dioxaheptyl) amine (0.1 g, 0.0003 mole), tetrahydrofuran (100 cm$^3$) and sodium amide (11.7 g, 0.3 mole) were successively charged to a flask which had previously been purged with nitrogen. The reaction mixture was stirred and heated at 50°–60° C. under nitrogen for 2 hours. The product, after work up as described in Example 3, was found to contain 3.3 g of 3,4-dibromothiophene, a yield of 13%.

EXAMPLE 12

Preparation of 3-bromothiophene using hexabromobenzene

Hexabromobenzene (9.1 g 0.017 mole), tris (3,6-dioxaheptyl) amine (0.1 g, 0.0003 mole), thiophene (100cm$^3$) and sodium amide (11.7 g, 0.3 mole) were successively charged to a flask which had previously been purged with nitrogen. The mixture was stirred and heated under nitrogen at 50°–60 C. for 6 hours. The product, after work up as described in Example 3, was found to contain 0.47 g 3-bromothiophene and 0.06 g 2-bromothiophene. The yield on the assumption that one bromine only of the hexabromobenzene is utilised is 17% and the monobromothiophenes were in the ratio of 11 parts 2-bromothiophene to 89 parts 3 bromothiophene.

We claim:

1. A process for the preparation of thiophene derivative which is substituted at the beta-position by a bromine atom, which comprises reacting the corresponding beta-unsubstituted thiophene with an aromatic compound which is substituted with a bromine atom, in the presence of an alkali metal amide and a catalyst which is capable of forming a complex with the cation of the alkali metal amide, at a temperature in the range of from 10° to 90° C.

2. A process as claimed in claim 1, in which the aromatic compound is a thiophene derivative.

3. A process as claimed in claim 2, in which the aromatic compound is 2-bromothiophene or 2,5-dibromothiophene.

4. A process as claimed in any one of claims 1 to 3, in which the beta-unsubstituted thiophene is thiophene.

5. A process as claimed in any one of claims 1 to 3, in which the beta-unsubstituted thiophene and the aromatic compound are the same compound.

6. A process as claimed in any one of claims 1 to 3, in which the alkali metal amide is a sodium or potassium amide.

7. A process as claimed in any one of claims 1 to 3, in which the catalyst is a compound of general formula

$$R^1\text{-(O-CHR}^2\text{-CHR}^3)_m\text{CHR}^4\text{-CHR}^5)_3\text{N} \qquad (I),$$

in which $R^2$, and $R^3$, $R^4$ and $R^5$ are independently selected from a hydrogen atom and an alkyl group having up to 4 carbon atoms; $R^1$ represents an alkyl, cycloalkyl phenyl, alkylphenyl or phenylalkyl group in which an alkyl or cycloalkyl group has up to 12 carbon atoms; and m is 0 or an integer from 1 to 10; or a compound of general formula

$$R^6\text{-(O-R}^8)_r\text{-O-R}^7 \qquad (II)$$

in which $R^6$ and $R^7$, which may be the same or different, each represents a hydrogen atom or an alkyl group having from 1 to 4 carbon atoms; in each O-$R^8$ unit, which may be the same or different, $R^8$ independently represents a group selected from CHR$^9$CHR$^{10}$ and CHR$^9$CHR$^{10}$CR$^{11}$R$^{12}$ in which R$^9$, R$^{10}$, R$^{11}$ and R$^{12}$ are independently selected from a hydrogen atom and alkyl group having from 1 to 4 carbon atoms; and r represents an integer of from 1 to 15.

8. A process as claimed in claim 7, in which the catalyst is tris (3,6-dioxaheptyl)amine.

9. A process as claimed in any one of claims 1 to 3, in which the molar ratio of beta-unsubstituted thiophene to aromatic compound is in the range of from 1:1 to 25:1.

10. A process as claimed in any one of claims 1 to 3, in which the temperature is in the range of from 40° to 70° C.

* * * * *

UNITED STATES PATENT AND TRADEMARK OFFICE
CERTIFICATE OF CORRECTION

PATENT NO. : 4,889,940

DATED : December 26, 1989

INVENTOR(S) : PETER R. GROSVENOR ET AL

It is certified that error appears in the above-identified patent and that said Letters Patent is hereby corrected as shown below:

Claim 7 (column 6, line 50), the formula should be $$(R^1-(O-CHR^2-CHR^3)_m-O-CHR^4-CHR^5)_3N \qquad (I)$$

Claim 7 (column 6, line 52), change "and $R^3$" to --$R^3$--.

Claim 7 (column 6, line 55), change "an" to --any--.

Signed and Sealed this

Twenty-seventh Day of November, 1990

*Attest:*

HARRY F. MANBECK, JR.

*Attesting Officer*     *Commissioner of Patents and Trademarks*